United States Patent [19]

Nishii et al.

[11] Patent Number: 5,363,455
[45] Date of Patent: Nov. 8, 1994

[54] OPTICAL INFORMATION PROCESSOR

[75] Inventors: Kanji Nishii, Osaka; Masami Ito, Moriguchi; Atsushi Hukui, Osaka, all of Japan

[73] Assignee: Matsushita Electric Industrial Co., Ltd., Osaka, Japan

[21] Appl. No.: 10,401

[22] Filed: Jan. 28, 1993

[30] Foreign Application Priority Data

Jan. 30, 1992 [JP] Japan .................. 4-014613

[51] Int. Cl.$^5$ .............................................. G06K 9/74
[52] U.S. Cl. ...................... 382/31; 359/561; 382/42
[58] Field of Search ............... 382/31, 42, 43; 359/559, 561

[56] References Cited

U.S. PATENT DOCUMENTS

| | | | |
|---|---|---|---|
| 4,384,210 | 5/1983 | Stauffer | 350/162.17 |
| 4,637,056 | 1/1987 | Sherman et al. | 382/42 |
| 4,767,171 | 8/1988 | Keil et al. | 350/46.10 |
| 4,925,261 | 5/1990 | Byckling et al. | 350/371 |
| 5,028,102 | 7/1991 | Ogura et al. | 382/31 |
| 5,175,775 | 12/1992 | Iwaki et al. | 382/47 |
| 5,216,541 | 6/1993 | Takesue et al. | 382/42 |
| 5,235,461 | 8/1993 | Kirsch et al. | 382/31 |
| 5,239,595 | 8/1993 | Takemura et al. | 382/31 |

FOREIGN PATENT DOCUMENTS 0460625  12/1991  European Pat. Off. .
2-132412  5/1990  Japan .

OTHER PUBLICATIONS

Yu et al., "Optical disk based joint transform correlator", *Applied Optics*, vol. 30, No. 8, Mar. 10, 1991, pp. 915–916.

Upatnieks, "Portable real–time coherent optical correlator", *Applied Optics*, vol. 22, No. 18, Jul. 1983, pp. 2798–2803.

*Primary Examiner*—Joseph Mancuso
*Attorney, Agent, or Firm*—Wenderoth, Lind & Ponack

[57] ABSTRACT

A visual recognition apparatus for use in, for example, a robot requires an optical information processor for performing image processing or image recognition. The optical information processor includes a first spatial light modulator for displaying an input image, a first lens having a front focal plane on which the first spatial light modulator is positioned, a second spatial light modulator for displaying at least one optical filter, a second lens having a front focal plane on which the second spatial light modulator is positioned, and a third lens having a front focal plane on which a rear focal plane of the second lens lies. The optical information processor also includes a beam splitter for combining together light transmitted through the first lens with light transmitted through the third lens, and a fourth lens having a front focal plane on which both a rear focal plane of the first lens and a rear focal plane of the third lens generally lie.

4 Claims, 3 Drawing Sheets

OPTICAL INFORMATION PROCESSOR

BACKGROUND OF THE INVENTION

1. Field of the Invention

The present invention relates generally to a visual recognition apparatus for use in, for example, a robot, and more particularly to an optical information processor used in the visual recognition apparatus for performing image processing or image recognition.

2. Description of the Prior Art

Recently, there have been strong demands in the field of image processing or image recognition for processing a large number of pixels faster than that hitherto accomplished. To this end, an optical information processor making use of a high-speed parallel operation has been developed.

Japanese Laid-open Patent Publication (unexamined) No. 2-132412 discloses an optical information processor as shown in FIG. 1. In FIG. 1, reference numeral 20 denotes a TV camera; reference numeral 21 denotes a first liquid crystal display for displaying an image picked up by the TV camera 21; reference numeral 22 denotes a laser diode; reference numeral 23 denotes a collimator lens for collimating light from the laser diode 22; and reference numeral 24 denotes a first lens. The first liquid crystal display 21 is positioned on a first focal plane of the first lens 24 adjacent the collimator lens 23. Reference numeral 25 denotes a second liquid crystal display positioned on a second focal plane of the first lens 24 opposite to the first focal plane.

Furthermore, reference numeral 26 denotes a ROM (read-only memory); reference numeral 27 denotes a second lens; and reference numeral 28 denotes a photodetector. the ROM 26 are stored data of computer-generated Fourier-transform holograms obtained as a result of a calculation performed using pixels of the second liquid crystal display as sampling points against a plurality of reference patterns. These data are indicative of data of applied voltages corresponding to the transmittance of the individual pixels of the second liquid crystal display 25. The second liquid crystal display 25 and the photodetector 28 are positioned on first and second, opposite focal planes of the second lens 27, respectively.

The above-described conventional optical information processor operates as follows.

An image of an object picked up by the TV camera 20 is initially displayed on the first liquid crystal display 21. The laser diode 22 applies to the first liquid crystal display 21 a coherent beam collimated by the collimator lens 23. Because the first liquid crystal display 21 is positioned on the first focal plane of the first lens 24 adjacent the collimator lens 23, a Fourier-transform image of the object optically transformed by the first lens 24 is formed on the second focal plane of the first lens 24 and, hence, on the second liquid crystal display 25.

When the data stored in the ROM 26 are applied to the second liquid crystal display 25, the transmittance of each of the pixels of the second liquid crystal display 25 is spatially modulated. As a result, each of the computer-generated Fourier-transform holograms of the specific reference patterns, which functions as an optical filter, is displayed on the second liquid crystal display 25.

Accordingly, on the second liquid crystal display 25, the Fourier-transform image, which has been optically transformed by the first lens 24 from the image of the object displayed on the first liquid crystal display 21, is superimposed on each of the Fourier-transform images.

Furthermore, because the second liquid crystal display 25 is positioned on the first focal plane of the second lens 27 adjacent the display 25, when the Fourier-transform image of the object coincides with that of a specific reference pattern, i.e., when both indicate the same object, a bright point appears on the second focal plane of the second lens 27 opposite to the first focal plane thereof and is subsequently detected by the photodetector 28. In this way, an optical image processing is performed wherein an optical filter, which takes the form of a computer-generated hologram and is displayed on the second liquid crystal display 25, functions as a matched filter.

The above optical information processor has, however, a problem in that the optical path is long for the following reasons, contributing to the size of the apparatus. Let the wavelength of the laser diode 22, the pixel pitch of the first liquid crystal display 21, and the diameter of a Fourier-transform image displayed on the second liquid crystal display 25 be denoted by λ, P, and D, respectively. In this case, the focal length f of the first lens 24 is given by $f = D \cdot P / \lambda$. When $P = 50$ μm, $\lambda = 0.8$ μm, and $D = 60$ mm, a lens having a focal length of 3,125 mm is required. Accordingly, as shown in FIG. 1, the distance between the first liquid crystal display 21 and the second liquid crystal display 25 results in $2 \cdot f = 6,250$ mm which is extremely long. In short, the pixel pitch P of a spatial light modulator such as, for example, a liquid crystal display is generally ten or more times greater than that of a photographic dry plate, and therefore, a long optical path is required. As a matter of course, the long optical path makes optical information processors large.

SUMMARY OF THE INVENTION

The present invention has been developed to overcome the above-described disadvantages and is intended to provide a compact optical information processor wherein an optical system has a comparatively short optical path.

In accomplishing the above and other objects, an optical information processor according to the present invention comprises a first spatial light modulator for displaying an input image, a first lens having a first focal plane on which the first spatial light modulator is positioned, a second spatial light modulator for displaying at least one optical filter, a second lens having a first focal plane on which the second spatial light modulator is positioned, and a third lens having a first focal plane on which a second focal plane of the second lens lies.

The optical information processor also comprises means for combining light transmitted through the first lens with light transmitted through the third lens, and a fourth lens having a first focal plane on which both a second focal plane of the first lens and a second focal plane of the third lens generally lie.

Another optical information processor of the present invention comprises a first spatial light modulator for displaying an input image, a first lens having a first focal plane on which the first spatial light modulator is positioned, a second lens having a first focal plane on which a second focal plane of the first lens lies, and a third lens having a first focal plane on which a second focal plane of the second lens lies.

The optical information processor further comprises a second spatial light modulator for displaying at least one optical filter, a fourth lens having a first focal plane on which the second spatial light modulator is positioned, and a fifth lens having a first focal plane on which a second focal plane of the fourth lens lies.

The optical information processor also comprises means for combining light transmitted through the third lens with light transmitted through the fifth lens, and a sixth lens having a first focal plane on which both a second focal plane of the third lens and a second focal plane of the fifth lens generally lie.

Because the optical information processor has the above-described structure, the optical path is considerably small, whereby the optical information processor is compact.

BRIEF DESCRIPTION OF THE DRAWINGS

The above and other objects and features of the present invention will become more apparent from the following description of preferred embodiments thereof with reference to the accompanying drawings, throughout which like parts are designated by like reference numerals, and wherein.

DETAILED DESCRIPTION OF THE PREFERRED EMBODIMENTS

Figure 1:
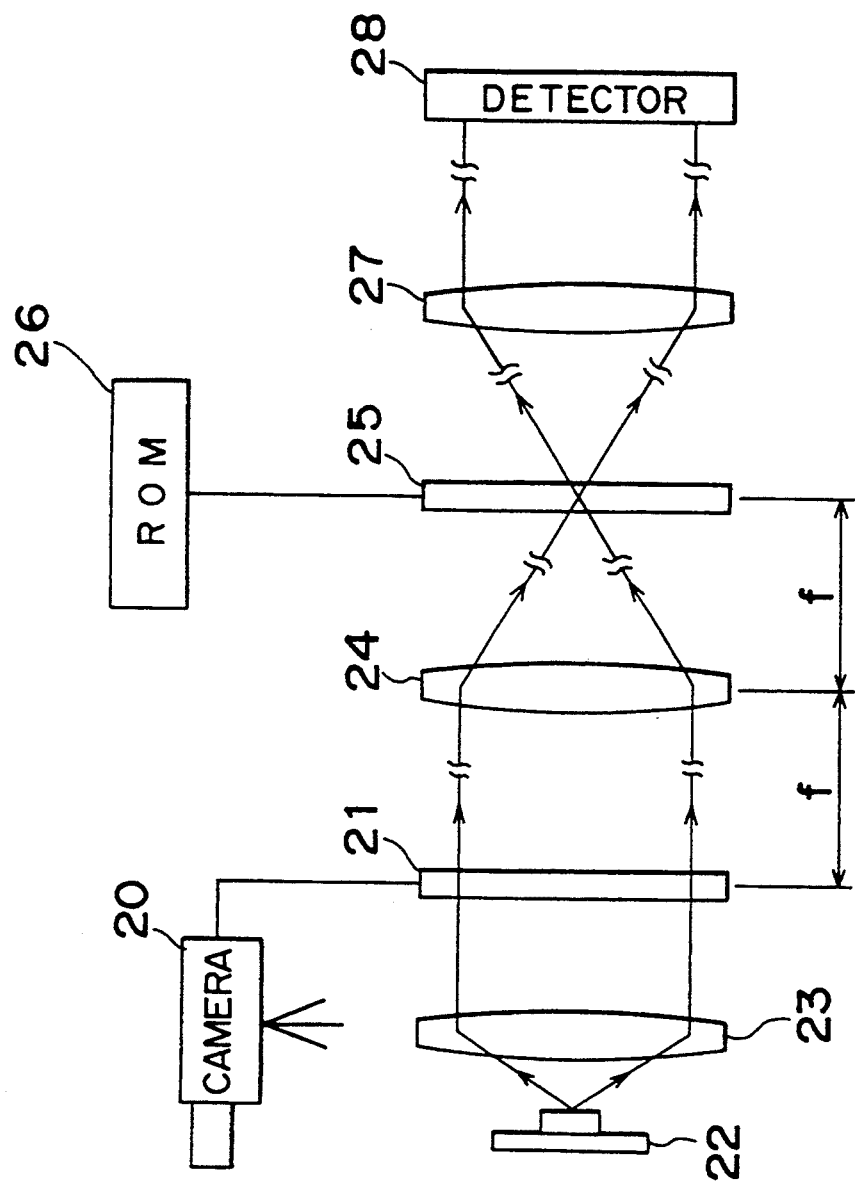
FIG. 1 is a schematic view of the prior art optical information processor.
Figure 2:
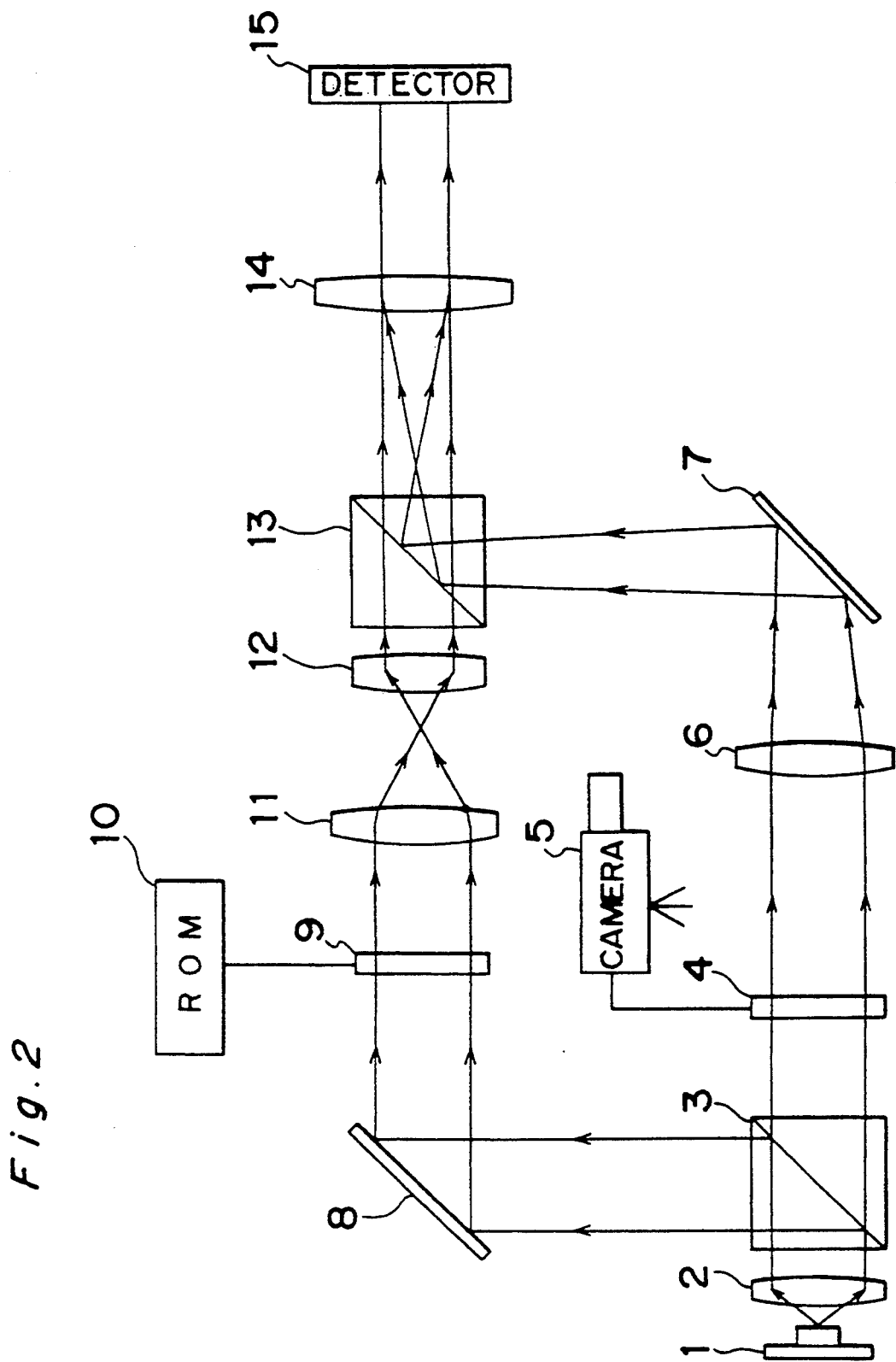
FIG. 2 is a schematic view of a first embodiment of an optical information processor showing to a first embodiment of the present invention.

Referring now to the drawings, there is shown in FIG. 2 an optical information processor according to the present invention. The optical information processor of FIG. 2 comprises a laser diode 1, a collimator lens 2 for collimating light from the laser diode 1, a first beam splitter 3 for splitting the collimated light from the collimator lens 2 into reflected light and transmitted light, a TV camera 5, and a first spatial light modulator 4 for displaying an image picked up by the TV camera 5. The first spatial light modulator 4 is positioned on a front focal plane of a first lens 6. An optical path of light having passed through the first lens 6 is changed by a first mirror 7. An optical path of light reflected by the first beam splitter 3 is changed by a second mirror 8. Light reflected by the second mirror 8 is directed to a second spatial light modulator 9. The second spatial light modulator 9 is operatively connected to a memory 10. This memory 10 stores data of computer-generated Fourier-transform holograms obtained as a result of calculations performed using pixels of the second spatial light modulator 9 as sampling points against a plurality of reference patterns. These data are indicative of data of applied voltages corresponding to the transmittance of the individual pixels of the second spatial light modulator 9.

The second spatial light modulator 9 is positioned on a front focal plane of a second lens 11 of which a back focal plane lies substantially on a front focal plane of a third lens 12. The second and third lenses 11 and 12 are so chosen that a focal length f2 of the second lens 11 is greater than a focal length f3 of the third lens 12. Accordingly, the second and third lenses 11 and 12 constitute an optical reduction system having a reduction ratio of f3/f2.

A second beam splitter 13 is provided as a combining means for combining together light transmitted through the first lens 6 and light transmitted through the third lens 12. A rear focal plane of the first lens 6 and that of the third lens 12 lie substantially on the same plane behind the second beam splitter 13. Behind the rear focal planes of the first and third lenses 6 and 12 are disposed a fourth lens 14 and a photodetector 15 positioned on a rear focal plane of the fourth lens 14.

The above-described optical information processor operates as follows.

An image of an object picked up by the TV camera 5 is initially displayed on the first spatial light modulator 4. A coherent beam emitted from the laser diode 1 is collimated by the collimator lens 2 and is then transmitted in part to the first spatial light modulator 4 via the first beam splitter 3. As a result, an optical Fourier-transform image of the object displayed on the first spatial light modulator 4 is formed on the rear focal plane of the first lens 6.

On the other hand, Fourier-transform images of the specific reference patterns are stored, as optical filters, in the memory 10. Therefore, when these data are supplied to the second spatial light modulator 9, the transmittance of each of the pixels thereof is spatially modulated, thereby displaying each of the computer-generated Fourier-transform holograms of the specific reference patterns on a region having a diameter of D. The computer-generated Fourier-transform holograms displayed on this region are projected on a reduced scale, onto another region having a diameter of Dx(f3/f2) and lying on the rear focal plane of the third lens 12, by the optical reduction system constituted by the second and third lenses 11 and 12.

Because the rear focal plane of the first lens 6 and that of the third lens 12 lie substantially on the same plane, the Fourier-transform image, which has optically been transformed by the first lens 6 from the object image displayed on the first spatial light modulator 4, is superimposed on each of the Fourier-transform images obtained as a result of calculations with respect to the specific reference patterns. This takes place on the common focal plane of the first and third lenses 6 and 12.

Because the common focal plane lies on the front focal plane of the fourth lens 14, when the Fourier-transform image of the object and that of a specific reference pattern coincide with each other, i.e., when both indicate the same object, a bright point appears on the rear focal plane of the fourth lens 14 and is detected by the photodetector 15. In this way, optical image processing is performed wherein an optical filter, which takes the form of a computer-generated hologram and is displayed on the second spatial light modulator 9, functions as a matched filter.

As described hereinabove, according to this embodiment, the optical filter is compact, namely smaller than the prior art by an corresponding to f3/f2. The focal length of the first lens 6 for optically performing Fourier transformation is as short as f3/f2.

For example, when f2=200 mm (F No.=3.3) and f3=50 mm (F No.=3.3), the reduction ratio becomes ¼. Accordingly, the focal length f1 of the first lens 6, which was, according to the prior art, required to be 3,125 mm, is 781 mm, one fourth of 3,125 mm. In this case, the distance between the second spatial light modulator 9 and the rear focal plane of the third lens 12 is 2×(200 mm+50 mm)=500 mm. Because these two optical paths extend parallel as shown in FIG. 2, the optical information processor according to this embodiment can be considerably small compared with the conventional one.

The optical reduction system constituted by the second and third lenses 11 and 12 has a longitudinal magnification of $(f3/f2)^2$. For example, when $f2=200$ mm and $f3=50$ mm, the longitudinal magnification becomes 1/16. In this case, fluctuations of the laser beam in a direction parallel to the optic axis in an optical system resulting from, for example, astigmatic difference of a laser diode, can be reduced to 1/16. A reduction in such fluctuations contributes to the precision of the optical information processor.

Figure 3:
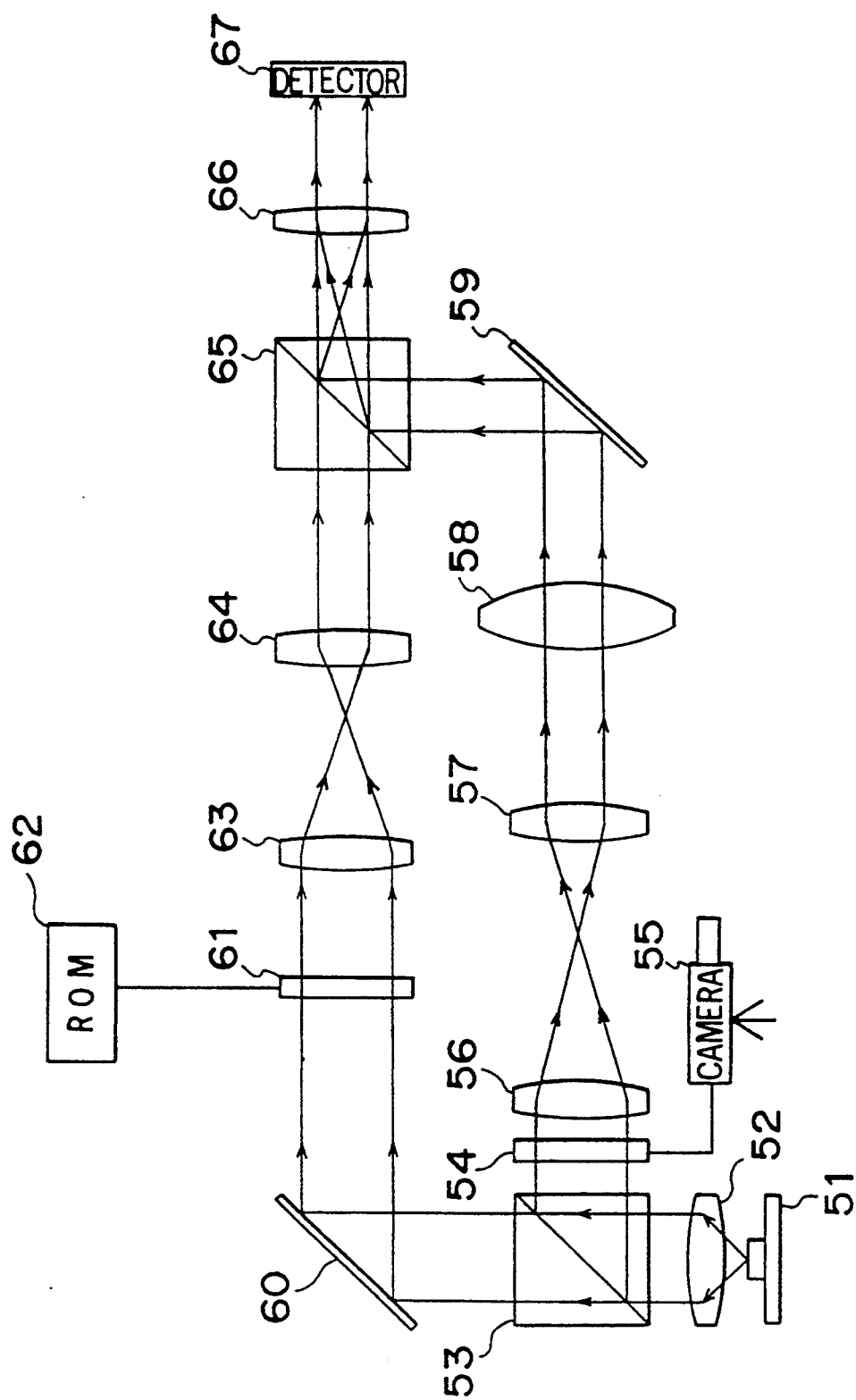
FIG. 3 is a view similar to FIG. 2, but according to a second embodiment of the present invention.

FIG. 3 depicts a second embodiment an optical information processor according to the present invention. This processor comprises a laser diode 51, a collimator lens 52 for collimating light from the laser diode 51, a first beam splitter 53 for splitting the collimated light from the collimator lens 52 into reflected light and transmitted light, a TV camera 55, and a first spatial light modulator 54 for displaying an image picked up by the TV camera 55.

The first spatial light modulator 54 is positioned on a front focal plane of a first lens 56. A rear focal plane of the first lens 56 lies substantially on the same plane as a front focal plane of a second lens 57. The first and second lenses 56 and 57 are so chosen that a focal length f1 of the former is greater than a focal length f2 of the latter. Accordingly, the first and second lenses 56 and 57 constitute an optical reduction system having a reduction ratio of f2/f1.

A rear focal plane of the second lens 57 lies substantially on the same plane as a front focal plane of a third lens 58. An optical path of light transmitted through the third lens 58 is changed by a first mirror 59. An optical path of light transmitted through the first beam splitter 53 is changed by a second mirror 60. Light reflected by the second mirror 60 is directed to a second spatial light modulator 61. The second spatial light-modulator 61 is operatively connected to a memory 62, which stores data of computer-generated Fourier-transform holograms obtained as a result of calculations performed using pixels of the second spatial light modulator 61 as sampling points against a plurality of reference patterns, as is the case with the first embodiment shown in FIG. 2. These data are indicative of data of applied voltages corresponding to the transmittance of the individual pixels of the second spatial light modulator 61.

The second spatial light modulator 61 is positioned on a front focal plane of a fourth lens 63, of which a rear focal plane lies substantially on the same plane as a front focal plane of a fifth lens 64. The fourth and fifth lenses 63 and 64 are so chosen that a focal length f4 of the former is greater than a focal length f5 of the latter. Accordingly, the fourth and fifth lenses 63 and 64 constitute an optical reduction system having a reduction ratio of f4/f5.

A second beam splitter 65 is provided as a combining means for combining together light transmitted through the third lens 58 and light transmitted through the fifth lens 64. A rear focal plane of the third lens 58 and that of the fifth lens 64 lie substantially on the same plane behind the second beam splitter 65. Behind the second beam splitter 65 is positioned a sixth lens 66 having a front focal plane lying substantially on the common rear focal plane of the third and fifth lenses 58 and 64. A photodetector 67 is positioned on a rear focal plane of the sixth lens 66.

The above-described optical information processor operates as follows.

An image of an object picked up by the TV camera 55 is initially displayed on the first spatial light modulator 54. A coherent beam emitted from the laser diode 51 is collimated by the collimator lens 52. The collimated light is in turn applied in part to the first spatial light modulator 54 via the first beam splitter 53. The optical reduction system constituted by the first and second lenses 56 and 57 reduces the scale of the object image, and the reduced image is projected on the rear focal plane of the second lens 57 at a reduction ratio of f2/f1. In other words, the pixel pitch P of the first spatial light modulator 54 is in effect reduced to Px(f2/f1). The third lens 58 forms an optical Fourier-transform image of the reduced object image on the rear focal plane thereof.

On the other hand, Fourier-transform images of the specific reference patterns are stored, as optical filters, in the memory 62. When these data are applied to the second spatial light modulator 61, the transmittance of each of individual pixels thereof is spatially modulated, thereby displaying each of the computer-generated Fourier-transform holograms of the specific reference patterns on a region having a diameter of D. The computer-generated Fourier-transform holograms displayed on this region are projected on a reduced scale onto another region, having a diameter of Dx(f5/f4) and lying on the rear focal plane of the fifth lens 64, by the optical reduction system constituted by the fourth and fifth lenses 63 and 64.

As mentioned previously, the rear focal plane of the third lens 58 and that of the fifth lens 64 lie substantially on the same plane. Accordingly, the Fourier-transform image, which has been optically transformed by the third lens 58 from the object image displayed on the first spatial light modulator 54 and projected on a reduced scale by the first and second lenses 56 and 57, is superimposed on each of the Fourier-transform images obtained as a result of calculations with respect to the specific reference patterns and similarly projected on a reduced scale by the fourth and fifth lenses 63 and 64. Such superimposition takes place on the common focal plane of the third and fifth lenses 58 and 64.

Because the common focal plane lies on the front focal plane of the sixth lens 66, when the Fourier-transform image of the object and that of a specific reference pattern coincide with each other, i.e., when both indicate the same object, a bright point appears on the rear focal plane of the sixth lens 66 and is detected by the photodetector 67. In this way, optical image processing is performed wherein an optical filter, which takes the form of a computer-generated hologram and is displayed on the second spatial light modulator 61, functions as a matched filter.

As described hereinabove, according to the second embodiment of the present invention, the size D of the optical filter is in effect reduced to f5/f4 by the optical reduction system constituted by the fourth and fifth lenses 63 and 64, whereas the pixel pitch P of the first spatial light modulator 54 is in effect reduced to f2/f1 by the optical reduction system constituted by the first and second lenses 56 and 57.

Accordingly, the focal length of the third lens 58 for optically performing Fourier transformation is as short as $(f2/f1) \times (f5/f4)$. For example, when $f1=160$ mm, $f2=40$ mm, $f4=160$ mm, and $f5=40$ mm, the reduction ratio becomes 1/16. Accordingly, the focal length f1 of the first lens 56, which was, according to the prior art, required to be 3,125 mm, will be 195 mm that is 1/16 of 3,125 mm.

In this case, the distance between the second spatial light modulator 61 and the rear focal plane of the fifth lens 64 is 2×(160 mm+40 mm)=400 mm, whereas the distance between the first spatial light modulator 54 and the rear focal plane of the third lens 58 is 2(160 mm+40 mm)+195 mm=595 mm. As shown in FIG. 3, because these two optical paths are parallel, the second embodiment of the optical information processor can be considerably small compared with the conventional one.

The optical reduction system constituted by the first and second lenses 56 and 57 has a longitudinal magnification of $(f2/f1)^2$ while the optical reduction system constituted by the fourth and fifth lenses 63 and 64 has a longitudinal magnification of $(f5/f4)^2$. For example, when f1=160 mm=f4 and f2=40 mm=f5, the longitudinal magnification becomes 1/16. In this case, fluctuations of the laser beam in a direction parallel to the optical axis of an optical system resulting from astigmatisms of the optics, can be reduced to 1/16. A reduction in such fluctuations contributes to the precision of the optical information processor.

In the above two embodiments, although each lens has been shown as a single lens, a doublet or a group of lenses may be used instead. Furthermore, although each spatial light modulator has been shown as a transmission type, any other suitable type of spatial light modulator such as, for example, a reflection type of liquid crystal display, may be used in place thereof.

Although the present invention has been fully described by way of examples with reference to the accompanying drawings, it is to be noted here that various changes and modifications will be apparent to those skilled in the art. Therefore, unless such changes and modifications otherwise depart from the spirit and scope of the present invention, they should be construed as being included therein.

What is claimed is:

1. An optical information processor comprising:
   a first spatial light modulator for displaying an input image;
   a first lens having first and second focal planes opposite to each other, said first spatial light modulator being positioned on the first focal plane of said first lens;
   a second spatial light modulator for displaying at least one optical filter;
   a second lens having first and second focal planes opposite to each other, said second spatial light-modulator being positioned on the first focal plane of said second lens;
   a third lens having first and second focal planes opposite to each other, the second focal plane of said second lens lying on the first focal plane of said third lens, and the focal length of said third lens to said first focal plane thereof being smaller than the focal length of said second lens to said second focal plane thereof;
   a fourth lens having first and second focal planes opposite to each other;
   combining means, disposed between the first focal plane of said fourth lens and both of said first and third lenses, for combining light transmitted through said first lens with light transmitted through said third lens; and
   both the second focal plane of said first lens and the second focal plane of said third lens lying on the first focal plane of said fourth lens such that the lights combined by said combining means are picked up by the fourth lens with sufficient focus.

2. An optical information processor as claimed in claim 1, wherein said first lens is disposed along a first optical path along which light is transmitted in the processor, and said second and said third lenses are disposed along a second optical path along which light is transmitted in the processor, said first and said second optical paths being parallel.

3. An optical information processor comprising:
   a first spatial light modulator for displaying an input image;
   a first lens having first and second focal planes opposite to each other, said first spatial light modulator being positioned on the first focal plane of said first lens;
   a second lens having first and second focal planes opposite to each other, the second focal plane of said first lens lying on the first focal plane of said second lens, and the focal length of said second lens to the first focal plane thereof being smaller than the focal length of the first lens to the second focal plane thereof;
   a third lens having first and second focal planes opposite to each other, the second focal plane of said second lens lying on the first focal plane of said third lens;
   a second spatial light modulator for displaying at least one optical filter;
   a fourth lens having first and second focal planes opposite to each other, said second spatial light-modulator being positioned on the first focal plane of said fourth lens;
   a fifth lens having first and second focal planes opposite to each other, the second focal plane of said fourth lens lying on the first focal plane of said fifth lens, and the focal length of said fifth lens to the first focal plane thereof being smaller than the focal length of said fourth lens to said second focal plane thereof;
   a sixth lens having first and second focal planes opposite to each other;
   combining means, disposed between the first focal plane of said sixth lens and both of said third and said fifth lenses, for combining light transmitted through said third lens with light transmitted through said fifth lens; and
   both the second focal plane of said third lens and the second focal plane of said fifth lens lying on the first focal plane of said sixth lens such that the light combined by said combining means is picked up by the sixth lens with sufficient focus.

4. An optical information processor as claimed in claim 3, wherein said first, said second and said third lenses are disposed along a first optical path along which light is transmitted in the processor, and said fourth, said fifth and said sixth lenses are disposed along a second optical path along which light is transmitted in the processor, said first and said second optical paths being parallel.

* * * * *